United States Patent
Gregg et al.

(10) Patent No.: US 9,474,598 B2
(45) Date of Patent: Oct. 25, 2016

(54) PROFILE REDUCTION SEAL

(71) Applicant: BOSTON SCIENTIFIC SCIMED, INC., Maple Grove, MN (US)

(72) Inventors: Peter W. Gregg, Santa Cruz, CA (US); David J. Paul, Scotts Valley, CA (US); Brian D. Brandt, San Jose, CA (US); Rajan Khokhar, Santa Cruz, CA (US)

( * ) Notice: Subject to any disclaimer, the term of this patent is extended or adjusted under 35 U.S.C. 154(b) by 868 days.

(21) Appl. No.: 13/645,727

(22) Filed: Oct. 5, 2012

(65) Prior Publication Data

US 2013/0090729 A1  Apr. 11, 2013

Related U.S. Application Data

(60) Provisional application No. 61/543,521, filed on Oct. 5, 2011.

(51) Int. Cl.
*A61F 2/24* (2006.01)
*A61L 27/14* (2006.01)

(52) U.S. Cl.
CPC ........... *A61F 2/2409* (2013.01); *A61F 2/2412* (2013.01); *A61F 2/2415* (2013.01); *A61F 2/2418* (2013.01); *A61L 27/14* (2013.01); *A61F 2210/0076* (2013.01); *A61F 2220/0075* (2013.01); *A61F 2250/0069* (2013.01)

(58) Field of Classification Search
CPC .. A61F 2/2418; A61F 2/2409; A61F 2/2412; A61F 2220/0016; A61F 2230/0054
USPC ...................................................... 623/2.38
See application file for complete search history.

(56) References Cited

U.S. PATENT DOCUMENTS

| | | | |
|---|---|---|---|
| 3,503,079 A | 3/1970 | Smith |
| 3,546,711 A | 12/1970 | Boyros |
| 3,551,913 A | 1/1971 | Shiley et al. |
| 3,570,014 A | 3/1971 | Hancock |
| 3,755,823 A | 9/1973 | Hancock |
| 3,983,581 A | 10/1976 | Angell et al. |
| 4,035,849 A | 7/1977 | Angell et al. |
| 4,340,977 A | 7/1982 | Brownlee et al. |
| 4,473,423 A | 9/1984 | Kolff |
| 4,484,365 A | 11/1984 | Murguet et al. |
| 4,490,859 A | 1/1985 | Black et al. |
| 4,510,628 A | 4/1985 | Kolff |
| 4,739,759 A | 4/1988 | Rexroth et al. |
| 5,258,023 A | 11/1993 | Reger |
| 5,326,372 A | 7/1994 | Mhatre et al. |
| 5,469,868 A | 11/1995 | Reger |
| 6,045,576 A | 4/2000 | Starr et al. |
| 6,254,636 B1 | 7/2001 | Peredo |

(Continued)

FOREIGN PATENT DOCUMENTS

EP  2119417 A2  11/2009
WO  2006127412 A1  11/2006

*Primary Examiner* — Yashita Sharma
*Assistant Examiner* — Tiffany Shipmon
(74) *Attorney, Agent, or Firm* — Seager, Tufte & Wickhem LLP (57) ABSTRACT

The disclosure pertains to profile reduction seals associated with heart valve replacements which may reduce or eliminate paravalvular regurgitation and methods of fabricating such seals. The generally cylindrical multilayer seals of the disclosure include a crown-like end and reinforcing elements which facilitate compression of the seal and associated device by minimizing bunching of the seal as it enters a delivery system.

16 Claims, 6 Drawing Sheets

(56) References Cited

U.S. PATENT DOCUMENTS

| | | |
|---|---|---|
| 6,558,417 B2 | 5/2003 | Peredo |
| 6,719,789 B2 | 4/2004 | Cox |
| 6,883,522 B2 | 4/2005 | Spence et al. |
| 6,951,573 B1 | 10/2005 | Dilling |
| 7,172,625 B2 | 2/2007 | Shu et al. |
| 7,175,659 B2 | 2/2007 | Hill et al. |
| 7,261,732 B2 | 8/2007 | Justino |
| 7,318,278 B2 | 1/2008 | Zhang et al. |
| 7,329,279 B2 | 2/2008 | Haug et al. |
| 7,381,219 B2 | 6/2008 | Salahieh et al. |
| 7,445,631 B2 | 11/2008 | Salahieh et al. |
| 7,524,331 B2 | 4/2009 | Birdsall |
| 7,575,594 B2 | 8/2009 | Sieracki |
| 7,670,370 B2 | 3/2010 | Hill et al. |
| 7,717,955 B2 | 5/2010 | Lane et al. |
| 7,748,389 B2 | 7/2010 | Salahieh et al. |
| 7,780,725 B2 | 8/2010 | Haug et al. |
| 7,819,915 B2 | 10/2010 | Stobie et al. |
| 7,824,442 B2 | 11/2010 | Salahieh et al. |
| 7,824,443 B2 | 11/2010 | Salahieh et al. |
| 7,892,281 B2 | 2/2011 | Seguin et al. |
| 7,959,666 B2 | 6/2011 | Salahieh et al. |
| 7,959,672 B2 | 6/2011 | Salahieh et al. |
| 7,988,724 B2 | 8/2011 | Salahieh et al. |
| 7,993,394 B2 | 8/2011 | Hariton et al. |
| 8,012,135 B2 | 9/2011 | Dann et al. |
| 8,029,564 B2 | 10/2011 | Johnson et al. |
| 8,048,153 B2 | 11/2011 | Salahieh et al. |
| 8,052,749 B2 | 11/2011 | Salahieh et al. |
| 8,075,611 B2 | 12/2011 | Millwee et al. |
| 8,136,659 B2 | 3/2012 | Salahieh et al. |
| 8,163,014 B2 | 4/2012 | Lane et al. |
| 8,172,892 B2 | 5/2012 | Chuter et al. |
| 8,182,528 B2 | 5/2012 | Salahieh et al. |
| 8,226,710 B2 | 7/2012 | Nguyen et al. |
| 8,231,670 B2 | 7/2012 | Salahieh et al. |
| 8,246,678 B2 | 8/2012 | Salahieh et al. |
| 8,252,052 B2 | 8/2012 | Salahieh et al. |
| 2002/0058994 A1 | 5/2002 | Hill et al. |
| 2002/0077698 A1 | 6/2002 | Peredo |
| 2003/0114924 A1 | 6/2003 | Moe |
| 2004/0015232 A1 | 1/2004 | Shu et al. |
| 2004/0030381 A1 | 2/2004 | Shu |
| 2004/0106990 A1 | 6/2004 | Spence et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143809 A1 | 6/2005 | Salahieh et al. |
| 2005/0197690 A1* | 9/2005 | Molaei .................. A61F 2/07 623/1.13 |
| 2005/0283231 A1 | 12/2005 | Haug et al. |
| 2006/0020327 A1* | 1/2006 | Lashinski et al. ............ 623/1.25 |
| 2006/0025854 A1 | 2/2006 | Lashinski et al. |
| 2006/0025855 A1 | 2/2006 | Lashinski et al. |
| 2006/0195184 A1 | 8/2006 | Lane et al. |
| 2006/0195185 A1 | 8/2006 | Lane et al. |
| 2006/0253191 A1 | 11/2006 | Salahieh et al. |
| 2006/0259137 A1 | 11/2006 | Artof et al. |
| 2006/0271172 A1 | 11/2006 | Tehrani |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0018214 A1 | 1/2007 | Ahn et al. |
| 2007/0027535 A1 | 2/2007 | Purdy, Jr. et al. |
| 2007/0129795 A1 | 6/2007 | Hill et al. |
| 2007/0162107 A1 | 7/2007 | Haug et al. |
| 2007/0203503 A1 | 8/2007 | Salahieh et al. |
| 2007/0244552 A1 | 10/2007 | Salahieh et al. |
| 2007/0282436 A1 | 12/2007 | Pinchuk |
| 2008/0033543 A1 | 2/2008 | Gurskis et al. |
| 2008/0086204 A1* | 4/2008 | Rankin .................. 623/2.38 |
| 2008/0125859 A1 | 5/2008 | Salahieh et al. |
| 2008/0234814 A1 | 9/2008 | Salahieh et al. |
| 2009/0240320 A1 | 9/2009 | Tuval et al. |
| 2010/0036484 A1 | 2/2010 | Hariton et al. |
| 2010/0082094 A1 | 4/2010 | Quadri et al. |
| 2010/0100176 A1 | 4/2010 | Elizondo et al. |
| 2010/0121434 A1* | 5/2010 | Paul et al. .................. 623/2.11 |
| 2010/0131054 A1 | 5/2010 | Tuval et al. |
| 2010/0137979 A1 | 6/2010 | Tuval et al. |
| 2010/0168844 A1 | 7/2010 | Toomes et al. |
| 2010/0191327 A1 | 7/2010 | Lane et al. |
| 2010/0249894 A1 | 9/2010 | Oba et al. |
| 2010/0249908 A1 | 9/2010 | Chau et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1 | 9/2010 | Zhang |
| 2010/0256752 A1 | 10/2010 | Forster et al. |
| 2010/0262231 A1 | 10/2010 | Tuval et al. |
| 2010/0280495 A1 | 11/2010 | Paul et al. |
| 2011/0000073 A1 | 1/2011 | O'Fallon et al. |
| 2011/0098802 A1 | 4/2011 | Braido et al. |
| 2011/0125258 A1 | 5/2011 | Centola |
| 2011/0166648 A1 | 7/2011 | Robin et al. |
| 2011/0172765 A1 | 7/2011 | Nguyen et al. |
| 2011/0213460 A1 | 9/2011 | Lashinski et al. |
| 2011/0218619 A1 | 9/2011 | Benichou et al. |
| 2011/0224781 A1 | 9/2011 | White |
| 2011/0230956 A1 | 9/2011 | White |
| 2011/0245918 A1 | 10/2011 | White |
| 2011/0257735 A1 | 10/2011 | Salahieh et al. |
| 2011/0276128 A1 | 11/2011 | Cao et al. |
| 2011/0276129 A1 | 11/2011 | Salahieh et al. |
| 2011/0319991 A1 | 12/2011 | Hariton et al. |
| 2012/0016469 A1 | 1/2012 | Salahieh et al. |
| 2012/0016471 A1 | 1/2012 | Salahieh et al. |
| 2012/0022629 A1 | 1/2012 | Perera et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0053683 A1 | 3/2012 | Salahieh et al. |
| 2012/0059454 A1 | 3/2012 | Millwee et al. |
| 2012/0078356 A1 | 3/2012 | Fish et al. |
| 2012/0078357 A1 | 3/2012 | Conklin |
| 2012/0089224 A1 | 4/2012 | Haug et al. |
| 2012/0095549 A1 | 4/2012 | Forster et al. |
| 2012/0136432 A1 | 5/2012 | Forster et al. |
| 2012/0143316 A1 | 6/2012 | Seguin et al. |
| 2012/0185039 A1 | 7/2012 | Tuval et al. |
| 2012/0226348 A1 | 9/2012 | Lane et al. |
| 2012/0232459 A1 | 9/2012 | Dann et al. |
| 2012/0245706 A1 | 9/2012 | Alavi et al. |
| 2012/0259409 A1 | 10/2012 | Nguyen et al. |

* cited by examiner

PROFILE REDUCTION SEAL

TECHNICAL FIELD

The present disclosure pertains to medical devices, and methods for manufacturing medical devices. More particularly, the present disclosure pertains to medical devices for delivering a replacement heart valve.

BACKGROUND

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure pertains to a profile reduction seal for a heart valve replacement comprising a multilayer, generally cylindrical seal body having a distal end, a proximal end, and a lumen therebetween; a plurality of reinforcing grommets disposed and distributed proximate the proximal end of the multilayer, generally cylindrical seal body; and a distal reinforcing band disposed proximate the distal end of the multilayer, generally cylindrical seal body, wherein the proximal end of the multilayer, generally cylindrical seal body comprises a plurality of alternating projections and recesses.

This disclosure also pertains to a method of forming a profile reduction seal for a heart valve replacement comprising positioning a cleaned, tapered seal-forming mandrel in a coating apparatus; applying a first coating composition comprising a carrier and at least one polymer to the cleaned tapered mandrel; removing the carrier from the first coating composition thereby forming a first coated mandrel; positioning a distal reinforcing band to encircle the first coated mandrel; positioning a plurality of grommets on the first coated mandrel; applying a second coating composition comprising a carrier and at least one polymer to the first coated mandrel, the distal reinforcing band, and the plurality of grommets; removing the carrier from the second coating composition thereby forming a second coated mandrel; applying a third coating composition comprising a carrier and at least one polymer to the first coated mandrel; removing the carrier from the third coating composition thereby forming a profile reduction seal precursor; confirming that the profile reduction seal precursor is fully formed and meets thickness specifications; trimming the profile reduction seal precursor to conform to dimensional specifications; and removing the profile reduction seal from the tapered seal-forming mandrel.

DETAILED DESCRIPTION

The following description should be read with reference to the drawings wherein like reference numerals indicate like elements throughout the several views. The drawings, which are not necessarily to scale, are not intended to limit the scope of the claimed invention. The detailed description and drawings illustrate example embodiments of the claimed invention.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments whether or not explicitly described unless clearly stated to the contrary.

This disclosure pertains to a profile reduction seal for a heart valve replacement comprising a multilayer, generally cylindrical seal body with a plurality of reinforcing grommets disposed and distributed proximate the proximal end of the seal body and a distal reinforcing band disposed proximate the distal end of the multilayer, generally cylindrical seal body. The grommets and band provide reinforcement for sutures or other attachment devices which affix the multilayer, generally cylindrical seal body to the anchoring element of a heart valve replacement. The seal serves to minimize or eliminate paravalvular regurgitation.

Figure 1:
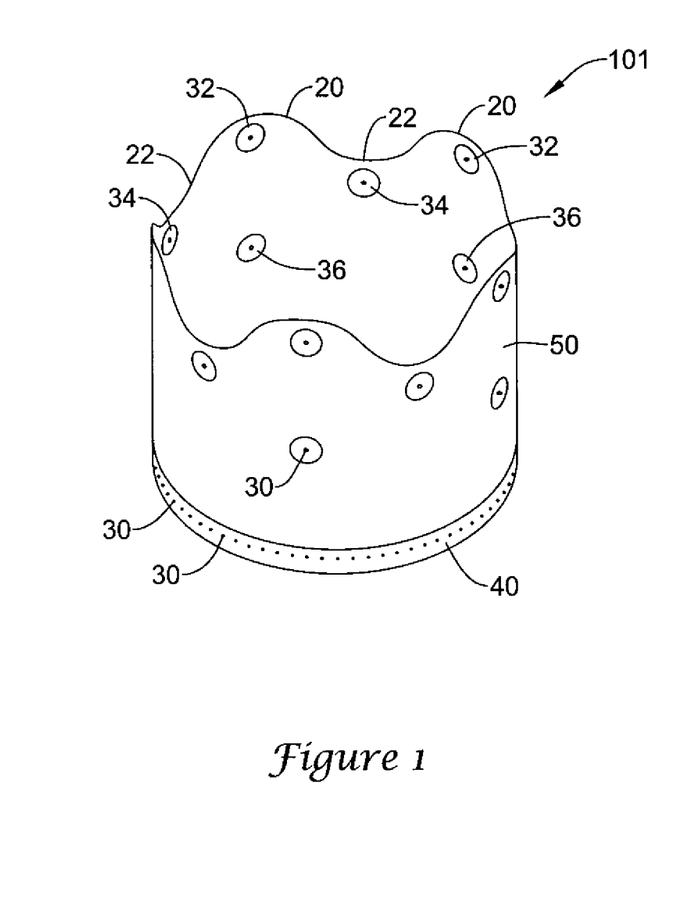
FIG. 1 illustrates an exemplary embodiment of the profile reduction seal of the disclosure.

Prior to introduction of the heart valve replacement into the patient's body, the heart valve replacement is compressed within a delivery system, a step which in prior art embodiments tended to produce undesirable bunching of the seal as the proximal end of the seal was reduced in diameter during insertion into the delivery system. The current design minimizes this bunching tendency by reducing the amount of material which is presented circumferentially at the leading edge of the seal as it initially enters the delivery system and gradually increasing the amount of material which is presented circumferentially as the seal 50 enters the delivery system (not shown) until the full circumferential amount of seal material is presented to the mouth of the delivery system being loaded. This may be accomplished by creating a series of alternating projections and recesses which resemble a crown at the proximal edge of the seal as illustrated in FIG. 1. Although the embodiment illustrated has five projections or crown points and five recesses, it will be readily appreciated that number of projections, and corresponding recesses, may be altered as desired.

In FIG. 1, the illustrated profile reduction seal for a heart valve replacement comprises a multilayer, generally cylindrical seal body 50, also referred to herein as a seal body or profile reduction seal 50, having projections 20 alternating with recesses 22 along the proximal edge of the seal body 50. The seal body 50 may include proximal reinforcing grommets 32, 34, 36 and a distal reinforcing band 40 which may be formed from a woven or nonwoven fabric and either incorporated within the interior of the multilayer seal body 50 or adhered to the surface thereof. The reinforcing materials provide tear resistance in the vicinity of sutures or other attachment devices which affix the profile reduction seal to an anchor element associated with the heart valve replacement. The distal reinforcement band 40 may be used to affix the distal end of the seal body 50 to the distal end of an anchor element associated with the heart valve replacement. In the illustrated embodiment, the grommets are distributed proximate the proximal edge of the seal body 50 as follows. At least some grommets 32 of the plurality of reinforcing grommets are disposed within projections 20 of the proximal end of the multilayer, generally cylindrical seal body 50 and proximate the proximate end of the projections 20. Although the grommets are depicted as circular and spaced slightly away from the edge this is not a necessary design feature. In some embodiments, the grommets 32 may be somewhat larger and may serve to stiffen the proximal tip of the projections to lessen curl which might otherwise allow one or more of the projections to catch on the mouth of the delivery system during compression. At least some of the grommets 34 of the plurality of reinforcing grommets are disposed within the multilayer, generally cylindrical seal body and proximate the recesses 22 of the proximal end of the multilayer, generally cylindrical seal body 50. In some embodiments, at least some of grommets 36 of the plurality of reinforcing grommets are disposed within the multilayer, generally cylindrical seal body 50 distal of the projections 20 of the proximal end of the multilayer, generally cylindrical seal body 50 and distal of the recesses 22 of the proximal end of the multilayer, generally cylindrical seal body 50.

In some embodiments, reinforcing grommets 32, 34, 36 include one or more perforations 30, said perforations 30 extending through both the reinforcing grommets 32, 34, 36 and the multilayer, generally cylindrical seal body 50. In the various embodiments, the reinforcing grommets 32, 34, 36 may comprise a woven fabric or a nonwoven fabric. In some such embodiments, the woven or nonwoven fabric may comprise polyester fibers.

In some embodiments, distal reinforcing band 40 also may include a plurality of perforations 30, said perforations 30 extending through both the distal reinforcing band 40 and the multilayer, generally cylindrical seal body 50. In the various embodiments, the reinforcing band 40 may comprise a woven fabric or a nonwoven fabric such as a polyester fiber fabric.

The profile reduction seals of this disclosure will have a "generally cylindrical" seal body 50. As the term "generally cylindrical" will be used in this specification and claims, it will be understood to include tubular bodies having one or more tapered sections which may be functionally tapered and/or which may taper to facilitate manufacturing of the profile reduction seals. In addition, "generally cylindrical" is to be interpreted as encompassing seals having transverse cross-sections which depart from strictly circular in an unconstrained condition. For example, a proximal end region may be fluted to encourage a predisposition to fold in an orderly manner as the seal body 50 enters the delivery system (not shown). See FIG. 2. The proximal end region may be fluted such that the projections 72 have an unconstrained radial position located somewhat inward from the mean radial position indicated by dashed line 70 while the recesses 74 have an unconstrained radial position located somewhat outward from the mean radial position indicated by dashed line 70. Of course, the roles of the projections and recesses may be reversed in some embodiments. Embodiments are also contemplated in which fluting is combined with tapered sections.

Figure 3:
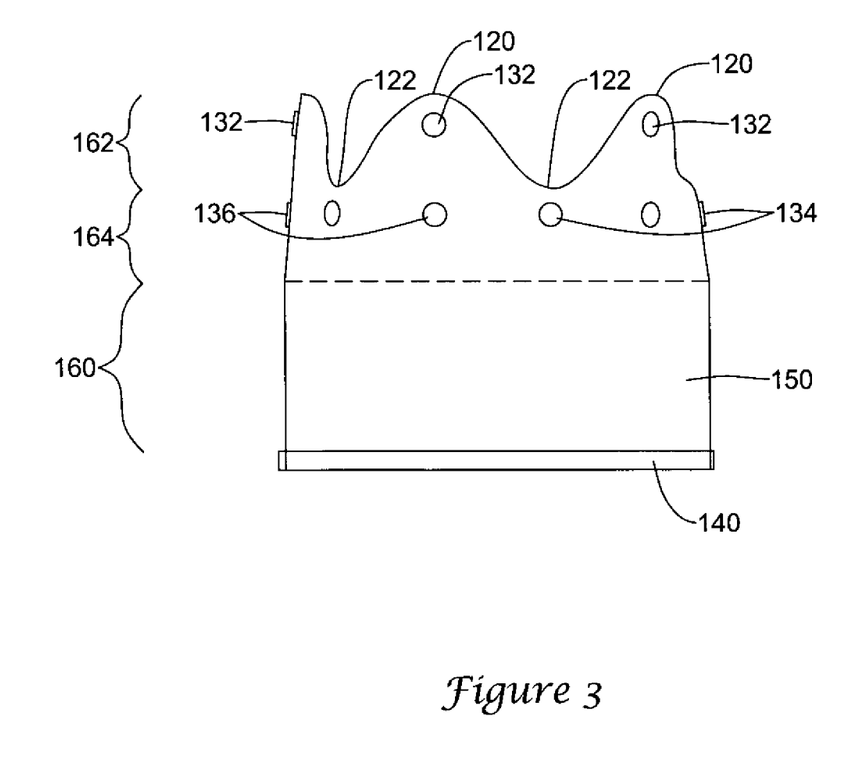
FIG. 3 illustrates a side view of another embodiment of the profile reduction seal of the disclosure.

In the non-limiting embodiment of FIG. 3, generally cylindrical profile reduction seal 150 comprises three longitudinal sections. Distal section 160 includes distal reinforcing band 140 and has a slight proximal taper which may facilitate manufacture of the seal body. Proximal section 162 includes the projections 120, recesses 122, and three pluralities of grommets 132, 134, and 136. Although the grommets 132, 134, and 136 are illustrated as being affixed to the outer surface of the seal body 150, they may equivalently be located within the multilayered structure of the seal body 150 or along the inner surface of the seal body if desired. The seal body of FIG. 3 also includes a third intermediate section 164 which extends the taper of distal section 162. In other embodiments, the intermediate section 164 may have a taper which differs from that of section 162 and 160 or it may be absent entirely. In addition to facilitating manufacturing of profile reduction seals 150, it is believed that the proximal taper of section 162 may result in a slight stretching of the profile reduction seal 150 in that region which may encourage the seal to lie relatively tightly against the anchoring element of the heart valve replacement during compression of the heart valve replacement within a delivery system due to elastic recovery.

Figure 4:
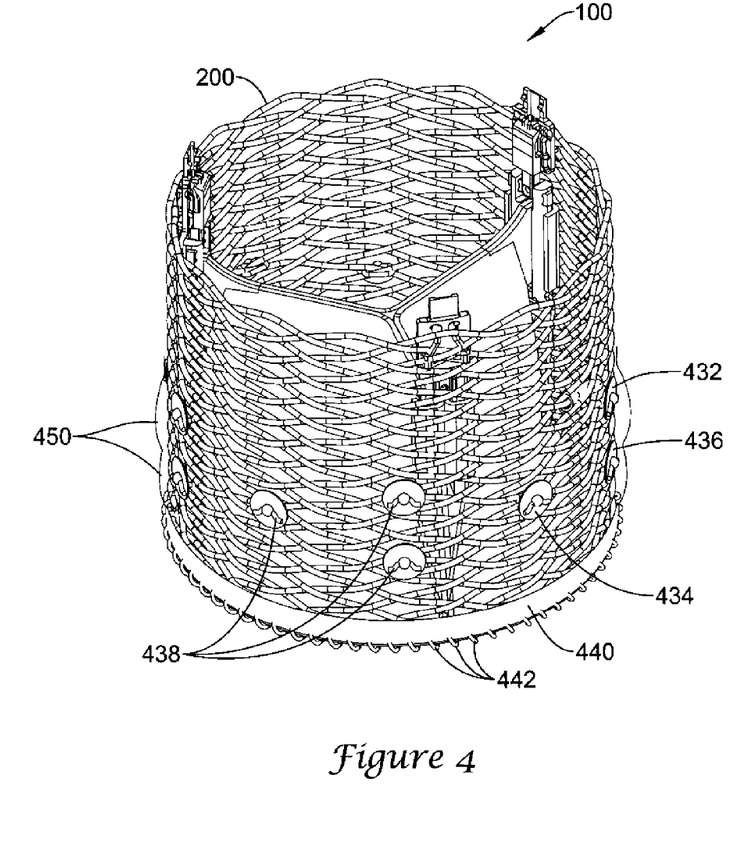
FIG. 4 illustrates an exemplary embodiment of the profile reduction seal of the disclosure deployed about a heart valve replacement.

FIG. 4 illustrates one embodiment of a profile reduction seal 450 disposed about anchor element 200 of heart valve replacement 100. In this embodiment seal 450 is secured to anchor element 200 by sutures 442 along distal reinforcing band 440 and by sutures 438 at grommets 432, 434, 436.

Figure 5:
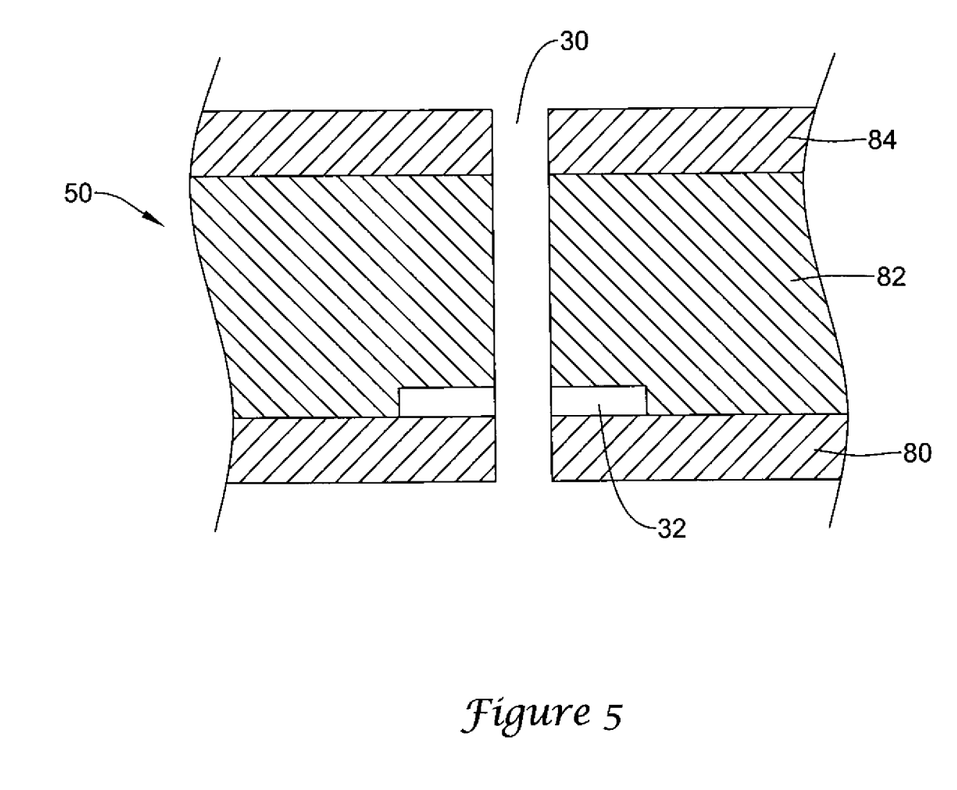
FIG. 5 illustrates a partial cross-section of an exemplary embodiment of a multilayer profile reduction seal of the disclosure.

The multilayer, generally cylindrical seal body 50, illustrated in partial cross-section in FIG. 5, may comprise a radially innermost layer 80 comprising a polycarbonate and a polyurethane; a radially outermost layer 84 comprising a polycarbonate and a polyurethane; at least one inner layer 82 disposed between the radially outermost layer 84 and the radially innermost layer 80, said at least one inner layer 82 comprising a polycarbonate and a polyurethane. In some embodiments, the modulus of elasticity of the inner layer 82 is less than the modulus of elasticity of the radially innermost outer layer 80 and the modulus of elasticity of the radially outermost outer layer 84. In other embodiments, the elongation to break of the inner layer 82 is greater than the elongation to break of the radially innermost outer layer 80 and the elongation to break of the radially outermost outer layer 84. Although the radially innermost outer layer 80 and the radially outermost outer layer 84 have been depicted as comprising the same material, it will be appreciated that they may be compositionally the same or different. In addition to the radially innermost outer layer 80, inner layer 82, and the radially outermost outer layer 84, the multilayer, generally cylindrical seal body 50 may also contain a reinforcing layer such as grommet 32 of FIG. 5. The reinforcing layer may comprise a woven or nonwoven fabric and may be positioned within or between the various layers. In some embodiments, a reinforcing layer or layers may be positioned on a radially innermost surface or radially outermost surface of the multilayer, generally cylindrical seal body 50. In other embodiments, reinforcing layers may be aligned and comprise more than one layer of the multilayer, generally cylindrical seal body 50. As noted elsewhere, reinforcing grommets and or bands may include perforations 30. In some embodiments, the perforations may extend completely through the multilayer, generally cylindrical seal body 50.

Figure 6:
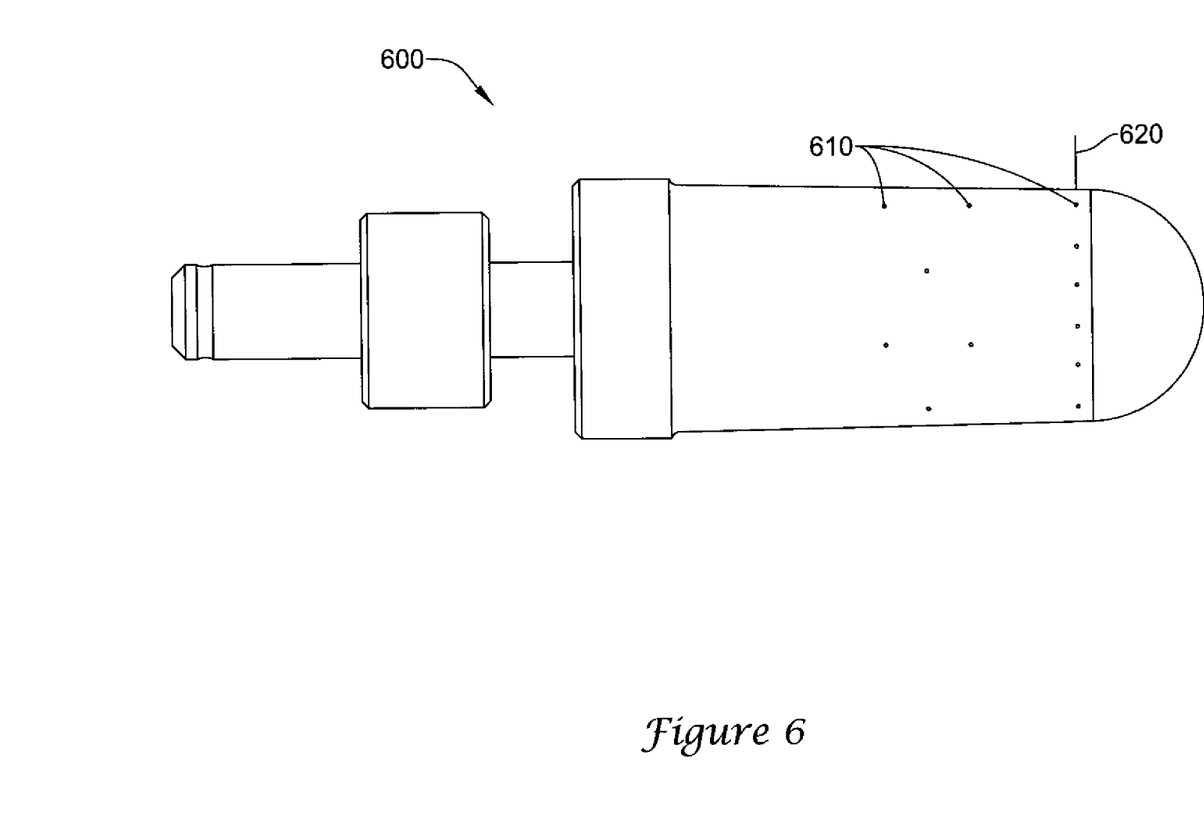
FIG. 6 illustrates a tapered mandrel suitable for the formation of a multilayer profile reduction seal of the disclosure.

The multilayer, generally cylindrical seal body 50 may be formed in a variety of ways, for example it may be formed by successive applications of a polymer solution to an appropriately shaped mandrel illustrated in FIG. 6. Following a careful cleaning of the mandrel 600, the mandrel may be mounted to an appropriate holding fixture in a spray booth. A first coating composition comprising a carrier and at least one polymer may be applied to the mandrel 600 and subsequently dried to form a first coated mandrel. In some embodiments, the first coating composition comprises a polycarbonate, a polyurethane, and a volatile carrier. The coating composition may be applied as a single layer or multiple layers to achieve the desired dried coating thickness. The plurality of grommets 32, 34, 36 and distal reinforcing band 40 may be positioned on the first coated mandrel, for example by inserting locating pins 620 in apertures 610 in the tapered mandrel 600 which align with corresponding perforations 30 provided in the grommets 32, 34, 36 and distal reinforcing band 40. In FIG. 6, only one pin 620 has been illustrated for clarity. In some instances, it may be desirable to secure the plurality of grommets 32, 34, 36 and distal reinforcing band 40 to the mandrel or to an underlying coating layer by applying a drop of a first coating composition, or other adhesive composition, to each item to ensure that it remains properly positioned during subsequent processing. Grommets 32, 34, 36 and distal reinforcing band 40 may be formed from a woven or nonwoven fabric. In some embodiments, the fabric may be a polyester fiber fabric.

A second coating composition comprising a carrier and at least one polymer may be applied to the first coated mandrel, the distal reinforcing band, and the plurality of grommets. In some embodiments, the second coating composition comprises a polycarbonate, a polyurethane, and a volatile carrier. The carrier of the second coating composition may be removed, thereby forming a second coated mandrel. The second coating composition may be applied as a single layer or as multiple layers to achieve the desired dried coating thickness. In some embodiments, the second coating composition may be different from the first coating composition. In other embodiments, the second coating composition may be the same as the first coating composition.

A third coating composition comprising a carrier and at least one polymer may be applied to the second coated mandrel. In some embodiments, the third coating composition comprises a polycarbonate, a polyurethane, and a volatile carrier. The carrier of the third coating composition may be removed thereby forming a profile reduction seal precursor. The third coating composition may be applied as a single layer or multiple layers to achieve the desired dried coating thickness. In some embodiments, the third coating composition may be different from the first coating composition. In other embodiments, the third coating composition may be the same as the first coating composition. In yet other embodiments, the third coating composition may be different from the second coating composition. In still other embodiments, the third coating composition may be the same as the second coating composition.

Following removal of the carrier from the third coating composition, the profile reduction seal precursor may be inspected to ensure that the profile reduction seal precursor is fully formed and meets thickness specifications. The profile reduction seal precursor may then be trimmed, for example by laser cutting, to conform to dimensional specifications; and removed from the tapered seal-forming mandrel thereby forming a profile reduction seal. In some embodiments, at least some of the perforations in one or both of the distal reinforcing band and the plurality of grommets 32, 34, 36 may be formed by laser cutting. In other embodiments, at least some of the grommets may be formed by a laser cutting operation performed on a profile reduction seal precursor. For example, grommets 32 may be added to the multilayer, generally cylindrical seal, in a step not illustrated, as a proximal band resembling distal reinforcing band 40. Subsequent laser cutting of the profile reduction seal precursor would then simultaneously form grommets 32 by removing the portions of the band located between the projections 20.

In some of the above embodiments, coating compositions may be selected to provide a relatively stiff dried polymer such as a dried polymer having a Shore D hardness of about 55. In other embodiments above, coating compositions may be selected to provide a relatively elastomeric dried polymer such as a dried polymer having a Shore A hardness of about 80. For example, the first and third dried polymer layers may have a Shore D hardness of 55 and the second layer may have a Shore A hardness of 80.

Although in the example above three polymer layers were employed, it will be appreciated that a greater or lesser number of layers may be employed and that each of the three or more layers may comprise two or more sublayers. Additionally, although the plurality of grommets and the distal reinforcing band were positioned between the first and second coating layers in the example, they could have been positioned elsewhere within the profile reduction seal including within a layer, or on the radially innermost or radially outermost surface of the profile reduction seal. It will also be appreciated that it is not necessary that the grommets and distal reinforcing band all be located at the same radial position within the profile reduction seal. As noted herein, in some embodiments, instead of a single grommet disposed at each location, more than one grommet may be disposed at each location and distributed at various aligned locations within the profile reduction seal to provide additional strength. Similarly more than a single distal reinforcing band may be incorporated, for example a first band may be positioned between a first and second layer of the multilayer, generally cylindrical seal body and a second band may be positioned between a second and third layer of the multilayer, generally cylindrical seal body.

Figure 2:
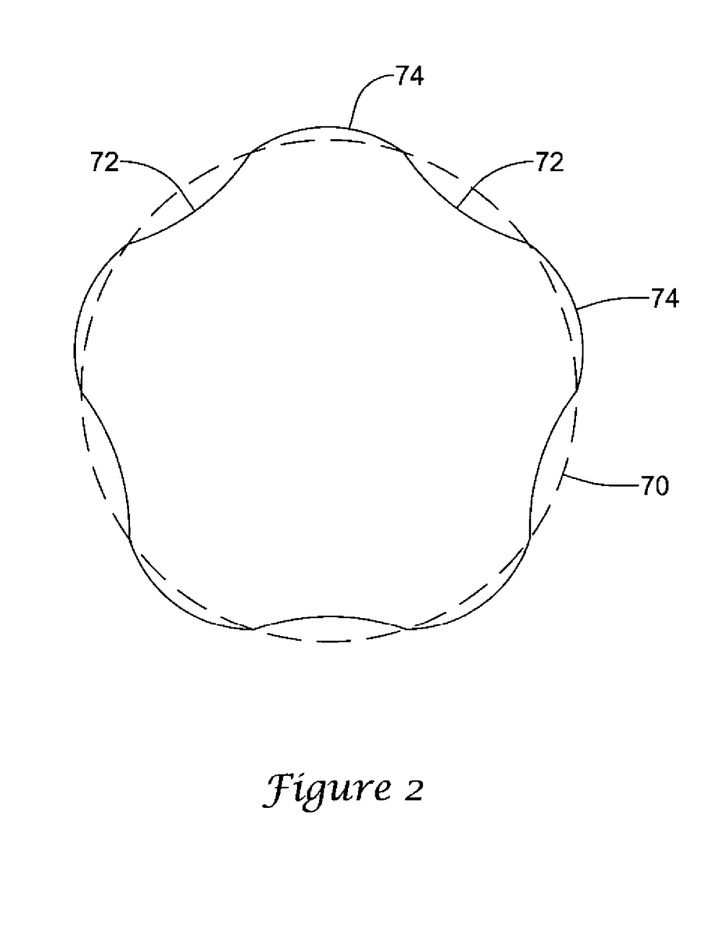
FIG. 2 illustrate a transverse cross-section of one embodiment of the profile reduction seal of the disclosure.

The mandrel 600 of FIG. 6 includes a taper which results in a profile reduction seal having a slightly smaller diameter proximal end compared to the diameter of the distal end. The taper allows the profile reduction seal to be removed from the mandrel with relative ease upon completion of the fabrication process. The smaller proximal diameter of the profile reduction seal tends to cause the proximal projections to lie more firmly against the anchor element of the replacement heart valve. In some embodiments, the surface of the mandrel may be textured, for example by bead blasting, to create a profile reduction seal having a lower apparent contact area. In combination with the selection of a relatively hard outer layer, a textured seal surface is believed to result in a lower friction surface. In other embodiments, the mandrel may include two or more regions having different degrees of taper in order to produce, for example, the profile reduction seal of FIG. 3. Yet other mandrels may include proximal grooves in the region of the crown-like projections and recesses. Such grooves may be broad and shallow to produce a transverse cross section which is fluted or undulated as illustrated in FIG. 2. In still further embodiments, the grooves may be narrow to produce a ribbed structure near or along the proximal edge of the resulting profile reduction seal. Of course, various tapers and/or grooving may be combined in a single mandrel if desired.

Although the illustrative examples described above relate to a profile reduction seal for a heart replacement valve, similar seals may be fabricated and attached to a variety of other implantable devices such as, for example, stents and aneurysm plugs. In such embodiments, the forming mandrel may have a different geometry and different polymers may be selected for the multiple layers.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed is:

1. A profile reduction seal for a heart valve replacement comprising:
    a multilayer, generally cylindrical seal body having a distal end, a proximal end, and a lumen therebetween;
    a plurality of reinforcing grommets disposed and distributed proximate the proximal end of the multilayer, generally cylindrical seal body; and
    a distal reinforcing band disposed proximate the distal end of the multilayer, generally cylindrical seal body;
    wherein the plurality of reinforcing grommets are embedded between layers of the multilayer, generally cylindrical seal body.

2. The profile reduction seal of claim 1, wherein the plurality of reinforcing grommets include one or more perforations, said one or more perforations extending through both the plurality of reinforcing grommets and the multilayer, generally cylindrical seal body.

3. The profile reduction seal of claim 1, wherein distal reinforcing band includes a plurality of perforations, said plurality of perforations extending through both the distal reinforcing band and the multilayer, generally cylindrical seal body.

4. The profile reduction seal of claim 1, wherein the multilayer, generally cylindrical seal body comprises a radially innermost outer layer comprising a polycarbonate and a polyurethane.

5. The profile reduction seal of claim 1, wherein the multilayer, generally cylindrical seal body further comprises a radially outermost outer layer comprising a polycarbonate and a polyurethane.

6. The profile reduction seal of claim 1, wherein the multilayer, generally cylindrical seal body comprises at least one inner layer disposed between a radially outermost outer layer and a radially innermost outer layer, said at least one inner layer disposed between the radially outermost outer layer and the radially innermost outer layer.

7. The profile reduction seal of claim 6, wherein the at least one inner layer disposed between the radially outermost outer layer and the radially innermost outer layer has a modulus of elasticity less than the modulus of elasticity of the radially innermost outer layer and less than the modulus of elasticity of the radially outermost outer layer.

8. The profile reduction seal of claim 6, wherein the at least one inner layer disposed between the radially outermost outer layer and the radially innermost outer layer has an elongation to break greater than the elongation to break of the radially innermost outer layer and greater than the elongation to break of the radially outermost outer layer.

9. The profile reduction seal of claim 1, wherein the plurality of reinforcing grommets comprises a woven fabric.

10. The profile reduction seal of claim 1, wherein the distal reinforcing band comprises a woven fabric.

11. The profile reduction seal of claim 1, wherein the proximal end of the multilayer, generally cylindrical seal body comprises a plurality of alternating projections and recesses.

12. The profile reduction seal of claim 11, wherein at least some of the plurality of reinforcing grommets are disposed within the plurality of projections of the proximal end of the multilayer, generally cylindrical seal body.

13. The profile reduction seal of claim 11, wherein at least some of the plurality of reinforcing grommets are disposed within the multilayer, generally cylindrical seal body and proximate the recesses of the proximal end of the multilayer, generally cylindrical seal body.

14. The profile reduction seal of claim 11, wherein at least some of the plurality of reinforcing grommets are disposed within the multilayer, generally cylindrical seal body and distal of the plurality of projections of the proximal end of the multilayer, generally cylindrical seal body and distal of the recesses of the proximal end of the multilayer, generally cylindrical seal body.

15. The profile reduction seal of claim 1, wherein the multilayer, generally cylindrical seal body has an undulating transverse cross-section.

16. The profile reduction seal of claim 1, wherein the multilayer, generally cylindrical seal body has a fluted transverse cross-section.

* * * * *